United States Patent [19]
La Pointe

[11] Patent Number: 6,034,240
[45] Date of Patent: Mar. 7, 2000

[54] SUBSTITUTED AMINOMETHYLPHOSPHINES, COORDINATION COMPLEXES OF AMINOMETHYLPHOSPHINES AND THEIR SYNTHESIS

[75] Inventor: Anne Marie La Pointe, Cupertino, Calif.

[73] Assignee: Symyx Technologies, Inc., Santa Clara, Calif.

[21] Appl. No.: 09/037,162

[22] Filed: Mar. 9, 1998

[51] Int. Cl.[7] ............................. C07C 209/10; C07F 9/38
[52] U.S. Cl. ........................... 546/24; 546/255; 546/144; 564/12; 564/15; 564/16; 564/386; 558/116; 558/385
[58] Field of Search ................... 546/255, 22; 544/337, 544/232; 564/16, 15

[56] References Cited

U.S. PATENT DOCUMENTS

| | | | |
|---|---|---|---|
| 3,553,265 | 1/1971 | Maier | 260/570.5 |
| 5,576,460 | 11/1996 | Buchwald et al. | 564/386 |

OTHER PUBLICATIONS

Anders, E. et al. Synthesis. (1991) 12, 1221–1227.
Kellner, K. et al. Z. Chem. (1984) 24, 365–374.
Keller et al., "Die Mannich–Reaktion als Synthesekonzept in der Phosphinchemie," *Z.Chem*, 24 Jg. (1984) Ueft 10, pp. 365–375.
Grim et al., "the Synthesis and Characterization of Some Novel Polydentate Phosphorus–Nitrogen Ligands," *Tetrahedron Letters*, No. 31, pp. 2951–2953, 1973.
McLain, "Organometallic Crown Ethers. 1. Metal Acyl Binding to a Crown Ether Held Cation, "*J. Am. Chem. Soc.*, 1983, 105, 6355–6357.
Reetz et al., "β–Cyclodextrin–Modified Diphoshanes as Ligands for Supramolecular Rhodium Catalysts," *Angew. Chem. Int. Ed. Engl.*, 1997, 36, No. 8, pp. 865–867.
Abd–Ellah et al., "Synthesis and Reactivity of Some Organophoshorus Derivatives of Schiff Bases," *Gazzetta Chimica Italiana*, 118 pp. 141–143 (1988).
Abd–Ellah et al., "Synthesis and Characterization of Some New Complexes of Phosphine Schiff Base Derivatives," *Proc. Indian Natn. Sci. Acad.*, vol. 55, No. 4, pp. 678–682 (1989).
Arbuzov et al., "Reaction of Dihydroxymethyl Phenylphosphine with Isobutyl Ester of Diphenylboric Acid in the Presence of Ritriles," *Izv. Akad. Nak. SSSR, Ser. Khi*, vol. 3, pp. 676–679 (1982).
Heinicke, et al., "Synthesis of 1,3–Azaphopholines–1" *Z. Chem*, vol. 26, No. 1, pp. 407–408 (1986).
Arbuzov et al., "Synthesis and Structure of 1,5–Diaza–3, 7–Diphosphacyclooctanes" *Izv. Akad. Nak. SSSR, Ser. Khi*, vol. 8, pp. 1846–1850 (1983).
Kamikawa et al., (1998), J. Org. Chem. 63: 8407–8410 Palladium–Catalyzed Amination of Aryl Bromides Utilizing Arene–Chromium Complexes as Ligands.
LaPointe, A.M. (1999) J. Comb. Chem. 1: 101–104 Parallel Synthesis of Aminomethylphosphine Ligands.
Shirakawa et al., (1997) Terahederon Letters 38 (21): 3759–3762 An Iminophoshine–Palladium Catalyst for Cross–Coupling of Aryl Halides with Organostannanes.

*Primary Examiner*—Mukund J. Shah
*Assistant Examiner*—Pavanaram K Sripada

[57] ABSTRACT

Novel aminomethylphosphine ligands have particular substituents on the central carbon atom. Such ligands form coordination complexes that may be catalysts for the polymerization of monomers or other catalytic induced reactions.

7 Claims, No Drawings

SUBSTITUTED AMINOMETHYLPHOSPHINES, COORDINATION COMPLEXES OF AMINOMETHYLPHOSPHINES AND THEIR SYNTHESIS

FIELD OF THE INVENTION

The present invention generally relates to the field of catalysis. In particular, this invention relates to new compounds that are useful as ligands for organometallic complexes that are catalysts. The invention also relates to combinatorial chemistry in that combinatorial techniques were used in connection with this invention.

BACKGROUND OF THE INVENTION

Ancillary ligand stabilized metal complexes (e.g., organometallic complexes) are useful as catalysts, additives, stoichiometric reagents, monomers, solid state precursors, therapeutic reagents and drugs. The ancillary ligand system comprises organic substituents that bind to the metal center (s), remain associated with the metal center(s), and therefore provide an opportunity to modify the shape, electronic and chemical properties of the active metal center(s) of the organometallic complex.

Certain organometallic complexes are catalysts for reactions such as oxidation, reduction, hydrogenation, hydrosilylation, hydrocyanation, hydroformylation, polymerization, carbonylation, isomerization, metathesis, carbon-hydrogen activation, cross-coupling, Friedel-Crafts acylation and alkylation, hydration, dimerization, trimerization, oligomerization, Diels-Alder reactions and other transformations. Organometallic complexes can be prepared by combining an ancillary ligand precursor with a suitable metal precursor in a suitable solvent at a suitable temperature.

One example of the use of organometallic complexes this is in the field of single-sited olefin polymerization catalysis. The active site typically comprises an ancillary ligand-stabilized, coordinatively unsaturated transition metal alkyl complex. Although a variety of such organometallic catalysts have been discovered over the past 15 years, the discovery process is laborious, entailing the individual synthesis of potentially catalytic materials and subsequently screening them for catalytic activity.

It is always a desire to discover new ligand systems that, once connected to a metal center, will catalyze reactions differently from known ligand systems. This invention provides new ancillary ligands that may be attached to a metal center. Once attached, such ligands modify the electronic and steric environment and may catalyze reactions differently from known systems.

SUMMARY OF THE INVENTION

The invention disclosed herein is a new ligand, which can be characterized by the general formula:

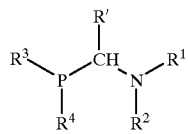

wherein each of $R^1$, $R^2$, $R^3$, and $R^4$ is, independently, selected from the group consisting of hydrogen, alkyl, substituted alkyl, aryl, substituted aryl, arylalkyl, substituted arylalkyl, acyl, halogen, amino, cyano, nitro, hydroxy, alkoxy, alkylamino, acylamino, silyl, germyl, stanyl, siloxy, phosphino, aryloxy, aryloxyalkyl, substituted aryloxyalkyl, heteroaryl, substituted heteroaryl, heteroarylalkyl, substituted heteroarylalkyl, heterocycles, substituted heterocycles, heterocyclicalkyl, substituted heterocyclicalkyl S-aryl and S-alkyl mercaptans and combinations thereof. Optionally, $R^1$ and $R^2$ are combined together to form a ring structure. Also optionally, $R^3$ and $R^4$ are combined together in a ring structure. $R^1$ is selected from the same group except that $R^1$ cannot be hydrogen.

The ligands of this invention are made in a novel method. The new method is particularly suitable for simultaneous or parallel synthesis of the ligands of this invention, however, serial synthesis is also possible. Generally, the aminomethylphosphines of this invention are prepared by a condensation reaction that combines an amine, a phosphine and an aldehyde, with a variety of substitutions on each, in tetrahydrofuran (THF) at about room temperature.

After synthesis, the ligand is combined with a metal precursor compound to form a coordination complex in a ligand exchange reaction. The resulting coordination complex is generally useful as a catalyst. For example, the coordination complex may be a single-site catalyst for the polymerization of olefins, diolefins or acetylenically unsaturated monomers, either alone or in combination. Depending on the structure of the compound, the catalyst may be activated for polymerization activity through the use of an activator or activating technique.

Thus, in one aspect of the invention, new ligands are provided that may be combined into a coordination complex useful as a catalyst.

In another aspect of this invention a new method of synthesis is provided that allows for easy synthesis of the new ligands, where the new procedure does not require refluxing or harsh solvents.

In a further aspect of this invention, new coordination complexes are provided that catalyze chemical reactions, including polymerization reactions.

In yet a further aspect of this invention, a polymerization process is described employing the coordination complexes of this invention as a or the only component of a catalyst system.

In still a further aspect of this invention, new polymers may be created through the use of a novel polymerization catalyst.

Further aspects of this invention will be evident to those of skill in the art upon review of this specification.

DETAILED DESCRIPTION OF THE INVENTION

The invention disclosed herein is a new ligand combined with metals to form coordination complexes that are useful as catalysts for chemical reactions, particularly polymerization reactions.

As used herein, the phrase "characterized by the formula" is not intended to be limiting and is used in the same way that "comprising" is commonly used. The term "independently selected" is used herein to indicate that the R groups, e.g., $R^1$, $R^2$, $R^3$, and $R^4$, can be identical or different (e.g. $R^1$, $R^2$, $R^3$, and $R^4$ may all be substituted alkyls or $R^1$ and $R^2$ may be a substituted alkyl and $R^3$ may be an aryl, etc.). Adjacent R-groups may be coupled to form cyclic structures. A named R group will generally have the structure that is recognized in the art as corresponding to R groups having that name. For the purposes of illustration, representative R groups as enumerated above are defined herein. These definitions are intended to supplement and illustrate, not preclude, the definitions known to those of skill in the art.

The term "alkyl" is used herein to refer to a branched or unbranched, saturated or unsaturated, monovalent hydrocarbon radical. When the alkyl group has from 1–6 carbon atoms, it is referred to as a "lower alkyl." Suitable alkyl radicals include, for example, methyl, ethyl, n-propyl, i-propyl, 2-propenyl (or allyl), n-butyl, t-butyl, i-butyl (or 2-methylpropyl), etc. As used herein, the term encompasses "substituted alkyls." In particular embodiments, alkyls have between 1 and 200 carbon atoms, between 1 and 50 carbon atoms or between 1 and 20 carbon atoms. "Substituted alkyl" refers to alkyl as just described including one or more functional groups such as lower alkyl, aryl, acyl, halogen (i.e., alkylhalos, e.g., $CF_3$), hydroxy, amino, phosphido, alkoxy, alkylamino, acylamino, acyloxy, aryloxy, aryloxyalkyl, mercapto, both saturated and unsaturated cyclic hydrocarbons, heterocycles and the like. These groups may be attached to any carbon of the alkyl moiety.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include substituted or unsubstituted phenyl, naphthyl, biphenyl, diphenylmethyl and benzophenone among others. In particular embodiments, aryls have between 1 and 200 carbon atoms, between 1 and 50 carbon atoms or between 1 and 20 carbon atoms. "Substituted aryl" refers to aryl as just described including one or more functional groups such as lower alkyl, acyl, halogen, alkylhalos (e.g., $CF_3$), hydroxy, amino, phosphido, alkoxy, alkylamino, acylamino, acyloxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone.

The term "acyl" is used to describe a ketone substituent, —C(O)X, where X is alkyl or substituted alkyl, aryl or substituted aryl as defined herein.

The term "amino" is used herein to refer to the group —NXX', where X and X' may independently be hydrogen, lower alkyl, substituted lower alkyl, aryl, substituted aryl or acyl. When an amino group is bonded to a metal through the nitrogen atom, it is referred to as an "amido" ligand.

The term "alkoxy" is used herein to refer to the —OX group, where X is an alkyl, substituted lower alkyl, aryl, substituted aryl, wherein the substituted alkyl, aryl, and substituted aryl groups are as described herein. Suitable alkoxy radicals include, for example, methoxy, ethoxy, phenoxy, substituted phenoxy, benzyloxy, phenethyloxy, t-butoxy, etc.

As used herein, the term "phosphino" refers to the group —PXX', where X and X' may independently be hydrogen, lower alkyl, substituted lower alkyl, aryl, substituted aryl or acyl.

As used herein, the term "mercapto" defines moieties of the general structure $X—S—X^1$ wherein X and $X^1$ are the same or different and are alkyl, aryl or heterocyclic as described herein.

The term "saturated cyclic hydrocarbon" denotes groups such as cyclopropyl, cyclobutyl, cyclopentyl, etc. and substituted analogues of these structures.

The term "unsaturated cyclic hydrocarbon" is used to describe a monovalent nonaromatic group with at least one double bond, such as cyclopentene, cyclohexene, etc. and substituted analogues thereof.

The term "cyclopentadienyl" is used to describe an aromatic five carbon ring group, which may be attached via a carbon in the ring, an $\eta^5$ bond or any other type of bond that a cyclopentadienyl group is known to form.

The term "substituted cyclopentadienyl" is used to describe a cyclopentadienyl, as just described, that is substituted with one or more functional groups such as lower alkyl, acyl, halogen, alkylhalos (e.g., $CF_3$), hydroxy, amino, phosphido, alkoxy, alkylamino, acylamino, acyloxy, mercapto, etc. "Substituted cyclopentadienyl" is also used to cover situations where the substituent is bis-cyclopentadienyl group, such as ferrocene, tetramethylcyclopentadienyl-dimethylsilyl-pentamethylcyclopentadienyl, bis(tetramethylcyclopentadienyl)dimethylsilyl or other bis-cyclopentadienyl groups.

The term "heteroaryl" as used herein refers to aromatic rings in which one or more carbon atoms of the aromatic ring(s) are substituted by a heteroatom such as nitrogen, oxygen or sulfur. Heteroaryl refers to structures that may be a single aromatic ring, multiple aromatic ring(s), or one or more aromatic rings coupled to one or more nonaromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Heteroarylalkyl" defines a subset of "alkyl" wherein the heteroaryl group is attached through an alkyl group as defined herein.

"Substituted heteroaryl" refers to heteroaryl as just described wherein the heteroaryl nucleus is substituted with one or more functional groups such as lower alkyl, acyl, halogen, alkylhalos (e.g., $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defined by the term "substituted heteroaryl."

"Substituted heteroarylalkyl" refers to a subset of "substituted alkyls" as described above in which an alkyl group, as defined herein, links the heteroaryl group to the nucleus.

The term "heterocyclic" is used herein to describe a monovalent saturated or unsaturated nonaromatic group having a single ring or multiple condensed rings from 1–12 carbon atoms and from 1–4 heteroatoms selected from nitrogen, phosphorous sulfur or oxygen within the ring. Such heterocycles are, for example, tetrahydrofuran, morpholine, piperidine, pyrrolidine, etc.

The term "substituted heterocyclic" as used herein describes a subset of "heterocyclics" wherein the heterocycle nucleus is substituted with one or more functional groups such as alkyl, acyl, halogen, alkylhalos (e.g., $CF_3$), hydroxy, amino, alkoxy, alkylamino, acylamino, acyloxy, mercapto, etc.

The term "heterocyclicalkyl" defines a subset of "alkyls" wherein an alkyl group, as defined herein, links the heterocyclic group to the nucleus.

The term "substituted heterocyclicalkyl" defines a subset of "heterocyclic alkyl" wherein the heterocyclic nucleus is substituted with one or more functional groups such as lower alkyl, acyl, halogen, alkylhalos (e.g., $CF_3$), hydroxy, amino, alkoxy, alkylamino, acylamino, acyloxy, mercapto, etc.

The ligands of this invention can be characterized by the formula:

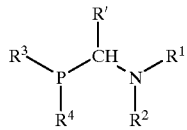

wherein each of $R^1$, $R^2$, $R^3$, and $R^4$ is, independently, selected from the group consisting of hydrogen, alkyl, substituted alkyl, aryl, substituted aryl, arylalkyl, substituted arylalkyl, acyl, halogen, amino, cyano, nitro, hydroxy, alkoxy, alkylamino, acylamino, silyl, germyl, stanyl, siloxy, phosphino, aryloxy, aryloxyalkyl, substituted aryloxyalkyl, heteroaryl, substituted heteroaryl, heteroarylalkyl, substituted heteroarylalkyl, heterocycles, substituted heterocycles, heterocyclicalkyl, substituted heterocyclicalkyl S-aryl and S-alkyl mercaptans and combinations thereof. Optionally, $R^1$ and $R^2$ are combined together to form a ring structure. Also optionally, $R^3$ and $R^4$ are combined together in a ring structure.

R' is selected from the group consisting of alkyl, substituted alkyl, aryl, substituted aryl, arylalkyl, substituted arylalkyl, acyl, halogen, amino, cyano, nitro, hydroxy, alkoxy, alkylamino, acylamino, silyl, germyl, stanyl, siloxy, phosphino, aryloxy, aryloxyalkyl, substituted aryloxyalkyl, heteroaryl, substituted heteroaryl, heteroarylalkyl, substituted heteroarylalkyl, heterocycles, substituted heterocycles, heterocyclicalkyl, substituted heterocyclicalkyl S-aryl and S-alkyl mercaptans and combinations thereof.

The substituents present on the basic ligand structure play an important role in determining the coordination geometry of the ligand to the metal center. While not wanting to be bound by any particular theory, such geometry differences may also affect the catalytic performance of the resulting coordination complex.

In more particular embodiments, $R^1$ and $R^2$ are, independently selected from the group consisting of alkyl, substituted alkyl, aryl, substituted aryl, cyclopentadienyl, substituted cyclopentadienyl, heteroaryl, substituted heteroaryl, heteroarylalkyl, substituted heteroarylalkyl, amino, alkoxy, saturated cyclic hydrocarbon, unsaturated cyclic hydrocarbon, heterocyclic, substituted heterocyclic, heterocyclicalkyl, substituted heterocyclicalkyl and combinations thereof. More preferably, $R^1$ and $R^2$ are, independently selected from the group consisting of alkyl, lower alkyl substituted alkyl, acyl substituted alkyl, halogen substituted alkyl, alkylhalo substituted alkyl, hydroxyl substituted alkyl, phosphino substituted alkyl, alkoxy substituted alkyl, alkylamino substituted alkyl, acylamino substituted alkyl, acyloxy substituted alkyl, mercapto substituted alkyl, lower alkyl substituted aryl, acyl substituted aryl, halogen substituted aryl, alkylhalo substituted aryl, hydroxyl substituted aryl, phosphino substituted aryl, alkoxy substituted aryl, alkylamino substituted aryl, acylamino substituted aryl, acyloxy substituted aryl, mercapto substituted aryl, cyclopentadienyl, substituted cyclopentadienyl, heteroaryl, substituted heteroaryl, heteroarylalkyl, substituted heteroarylalkyl, amino, alkoxy, saturated cyclic hydrocarbon, unsaturated cyclic hydrocarbon, heterocyclic, substituted heterocyclic, heterocyclicalkyl, substituted heterocyclicalkyl and combinations thereof. Specific examples from which either of $R^1$ and $R^2$ may be chosen are hydride, methyl, ethyl, propyl, isopropyl, benzyl, butyl, s-butyl, t-butyl, 2,4,6-trimethylphenyl, N,3,3'-trimethylaminopropyl, N,2,2'-trimethylaminoethyl, 3-cyano (N-methyl)ethyl, and 2-(2-pyridine)(N-methyl)ethyl.

In other embodiments, $R^1$ and $R^2$ are joined together to form a ring structure having up to 20 non-hydrogen atoms as the combined substituent. More particularly, when $R^1$ and $R^2$ are joined together, they are together selected from the group consisting of heterocyclic, substituted heterocyclic and substituted heterocyclicalkyl. Specific examples from which $NR^1R^2$ may together be chosen are morpholine, N-arylpiperazine (such as N-phenylpiperazine), N-alkylpiperazine (such as N-methylpiperazine and N-ethylpiperazine), and piperidine.

More particular embodiments $R^3$ and $R^4$ are where $R^3$ and $R^4$ are, independently selected from the group consisting of alkyl, substituted alkyl, aryl, substituted aryl, cyclopentadienyl, substituted cyclopentadienyl, heteroaryl, substituted heteroaryl, heteroarylalkyl, substituted heteroarylalkyl, amino, alkoxy, saturated cyclic hydrocarbon, unsaturated cyclic hydrocarbon, heterocyclic, substituted heterocyclic, heterocyclicalkyl, substituted heterocyclicalkyl and combinations thereof. More preferably, $R^3$ and $R^4$ are, independently selected from the group consisting of alkyl, lower alkyl substituted alkyl, acyl substituted alkyl, halogen substituted alkyl, alkylhalo substituted alkyl, hydroxyl substituted alkyl, phosphino substituted alkyl, alkoxy substituted alkyl, alkylamino substituted alkyl, acylamino substituted alkyl, acyloxy substituted alkyl, mercapto substituted alkyl, lower alkyl substituted aryl, acyl substituted aryl, halogen substituted aryl, alkylhalo substituted aryl, hydroxyl substituted aryl, phosphino substituted aryl, alkoxy substituted aryl, alkylamino substituted aryl, acylamino substituted aryl, acyloxy substituted aryl, mercapto substituted aryl, cyclopentadienyl, substituted cyclopentadienyl, heteroaryl, substituted heteroaryl, heteroarylalkyl, substituted heteroarylalkyl, amino, alkoxy, saturated cyclic hydrocarbon, -unsaturated cyclic hydrocarbon, heterocyclic, substituted heterocyclic, heterocyclicalkyl, substituted heterocyclicalkyl and combinations thereof. Specific examples from which either of $R^3$ and $R^4$ may be chosen are hydride, methyl, ethyl, propyl, isopropyl, benzyl, butyl, s-butyl, t-butyl, phenyl, cyclohexyl, 2,4,6-trimethylphenyl, methoxy, ethoxy, n-propoxy, i-propoxy, n-butoxy, s-butoxy, t-butoxy and phenoxy.

In other embodiments, $R^3$ and $R^4$ are joined together to form a ring structure having up to 20 non-hydrogen atoms as the combined substituent. More particularly, when $R^3$ and $R^4$ are joined together, they are together selected from the group consisting of heterocyclic, substituted heterocyclic and substituted heterocyclicalkyl.

In still further more specific embodiments, R' is selected from the group consisting of alkyl, substituted alkyl, aryl, substituted aryl, cyclopentadienyl, substituted cyclopentadienyl, heteroaryl, substituted heteroaryl, heteroarylalkyl, substituted heteroarylalkyl, amino, alkoxy, saturated cyclic hydrocarbon, unsaturated cyclic hydrocarbon, heterocyclic, substituted heterocyclic, heterocyclicalkyl, substituted heterocyclicalkyl and combinations thereof. More preferably, R' is selected from the group consisting of alkyl, lower alkyl substituted alkyl, acyl substituted alkyl, halogen substituted alkyl, alkylhalo substituted alkyl, hydroxyl substituted alkyl, phosphino substituted alkyl, alkoxy substituted alkyl, alkylamino substituted alkyl, acylamino substituted alkyl, acyloxy substituted alkyl, mercapto substituted alkyl, lower alkyl substituted aryl, acyl substituted aryl, halogen substituted aryl, alkylhalo substituted aryl, hydroxyl substituted aryl, phosphino substituted aryl, alkoxy substituted aryl, alkylamino substituted aryl, acylamino substituted aryl, acyloxy substituted aryl, mercapto substituted aryl, cyclopentadienyl, substituted cyclopentadienyl, heteroaryl, substituted heteroaryl, heteroarylalkyl, substituted heteroarylalkyl, amino, alkoxy, saturated cyclic hydrocarbon, unsaturated cyclic hydrocarbon, heterocyclic, substituted heterocyclic, heterocyclicalkyl, substituted heterocyclicalkyl and combinations thereof. Specific examples from which R' may be chosen are methyl, ethyl, propyl, isopropyl, benzyl, butyl, s-butyl, t-butyl, 2,4,6-trimethylphenyl, 4-trifluoromethylphenyl, ferrocenyl, 2-pyridyl, 2-cyanophenyl, 3-cyanophenyl and 2-(diphenylphosphino) phenyl.

The ligands of this invention are prepared by the condensation reaction of a phosphine, aldehyde and amine. The corresponding precursor compounds contain the desired substituents on the phosphorus, nitrogen and carbon atoms forming the backbone of the ligands of this invention. Thus, for example, if a pyridine substituent is desirable on the carbon atom, the starting aldehyde could be pyridine-2-carboxylaldehyde. By way of further example, if the desired substituents ($R^3$ and $R^4$) on the phosphorus are both phenyl, then the starting phosphine could be diphenylphosphine. Similarly, if the desired substituents on the nitrogen atom were methyl and benzyl ($R^1$ and $R^2$), then the starting amine could be N-methylbenzylamine. The condensation reaction preferably occurs at room temperature in a polar solvent, such as tetrahydrofuran (THF). But other solvents known to those skilled the art can be used. Illustrative examples of the ligands of this invention prepared by the above method include (tBu)(PhCH$_2$)NCH(Ph)P(C$_6$H$_{11}$)$_2$, (PhCH$_2$)(CH$_3$)NCH(ferrocenyl)P(C$_6$H$_{11}$)$_2${ferrocenyl=$^-$(C$_5$H$_4$)Fe(C$_5$H$_5$)}, (PhCH$_2$)(CH$_3$)NCH(Ph)P(tBu)$_2$, PhN(CH$_2$CH$_2$)$_2$NCH(Ph)P(t-Bu)$_2$, (2-pyridineCH$_2$CH$_2$)N(CH$_3$)CH(Ph)P(C$_6$H$_5$)$_2$, and (PhCH$_2$)(CH$_3$)NCH(4-(CF$_3$)C$_6$H$_4$)P(C$_6$H$_5$)$_2$.

Once the desired aminomethylphosphine ligand is formed, it may be reacted with a metal atom, ion or other metal precursor compound to form a metal-ligand coordination compound that may be a catalyst. The metal atom, ion or other metal precursor compound preferably combines with the ligands of this invention in a ligand exchange reaction to substitute the ligand of this invention for other ligands on the metal atom or ion, such as a chloride or methyl ligand. The metal may be chosen from any metal in the Periodic Table of Elements. In alternative embodiments, the metal is chosen from the group consisting of the transition metals of the Periodic Table of Elements. In more particular embodiments, the metal is chosen from the group consisting of Groups 3, 4, 5, 6, 7, 8, 9, 10 or 11 of the Periodic Table of Elements. Most preferred are Groups 4, 5, 6, 7, 8, 9 and 10 of the Periodic Table Elements, and specifically, Ti, Mn, Fe, Co, Ni and Pd.

In order to form the coordination complexes of this invention, the metals invention typically contain ligands that are exchanged for the aminomethylphosphine ligand of this invention. The ligands on the metals that leave in order for the coordination complexes of this invention to form preferably are selected from the group consisting of hydrogen, alkyl, substituted alkyl, halogen, saturated cyclic hydrocarbon, unsaturated cyclic hydrocarbon, heterocyclic, substituted heterocyclic, heterocyclicalkyl, substituted heterocyclicalkyl, ether and combinations thereof.

The aminomethylphosphine ligands of this invention may attach to the metal at one or more sites. Also, the aminomethylphosphine ligand can attach to the metal via one of the atoms in the backbone of the ligand (the phosphorus, carbon or nitrogen atom) or can attach via one of the substituents on the atoms in the backbone ($R^1$, $R^2$, $R^3$, $R^4$ or R'). In one preferred embodiment, the aminomethylphosphine ligands of this invention will bind to the metal via the nitrogen atom.

In another embodiment, the coordination complexes of this invention may be represented by the general formula:

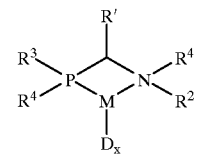

wherein $R^1$, $R^2$, $R^3$, $R^4$ and R' and M are defined as above. Additionally, the metal M may have one or more ligands $D_x$ where x is an integer from 0 to 3. Preferably, x is either 1 or 2. The ligand(s) D are selected, independently, from the group consisting of alkyl, substituted alkyl, aryl, substituted aryl, arylalkyl, substituted arylalkyl, halogen, amino, silyl, germyl, hydrido, oxo, imido, sulfido, cyclopentadienyl, substituted cyclopentadienyl, alkoxy, aryloxy and combinations thereof. Illustrative examples of coordination complexes are {(C$_6$H$_5$)$_2$PCH(Ph)N(CH$_3$)(CH$_2$Ph)}NiBr$_2$, {(C$_6$H$_5$)$_2$PCH(Ph)N(CH$_3$)(CH$_2$Ph)}Pd(CH$_3$)Cl, and {(C$_6$H$_5$)$_2$PCH(Ph)N(2,4,6-(CH$_3$)$_3$C$_6$H$_2$)}$_2$Ti(CH$_2$Ph)$_2$.

In an alternative embodiment, one or more of the ligands D is further bonded to the nitrogen or phosphorus atom in the aminomethylphosphine ligand via either the $R^2$ or $R^4$ group. In this embodiment, D is selected from the group consisting of alkyl, aryl, amino, alkoxy, aryloxy, aryloxyalkyl, heteroaryl, substituted heteroaryl, heteroarylalkyl substituted heteroarylalkyl, heterocycles substituted heterocycles and combinations thereof. An illustrative example of a coordination complex within this embodiment is [{(C$_6$H$_5$)$_2$PCH(Ph)N(CH$_3$)CH$_2$CH$_2$N(CH$_3$)$_2$}Pd(CH$_3$)]$^+$BAr'$_4^-$.

In another embodiment of the coordination complexes of this invention, the metal attaches to the aminomethylphosphine ligand through R' off of the carbon atom. This embodiment can be characterized by either of the following two general formulas:

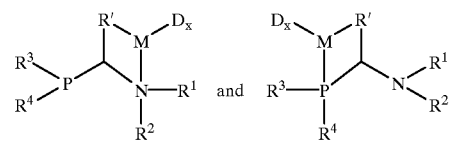

wherein $R^1$, $R^2$, $R^3$, $R^4$, R', D, M and x are as defined above. Illustrative examples of coordination complexes within these formula are {(C$_6$H$_5$)$_2$PCH(2-pyridine)N(CH$_3$)(CH$_2$Ph) }Pd(CH$_3$)Cl and {(C$_6$H$_5$)$_2$PCH(2-pyridine)N(CH$_3$)(CH$_2$Ph) }Pd(CH$_3$)(N≡CCH$_3$)$^+$BAr'$_4^-$.

Depending on the exact compounds chosen for $R^1$, $R^2$, $R^3$, $R^4$, R', D and M, alternative structures for the coordination complexes of this invention include:

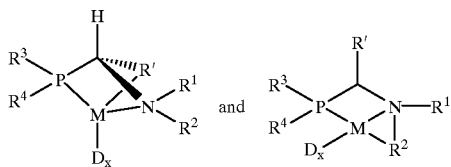

with $R^1$, $R^2$, $R^3$, $R^4$, R', D, M and x are as defined above.

Additional illustrative examples of the coordination complexes of this invention include $\{(CH_3)_2NCH_2CH_2N(CH_3)CH(Ph)P(C_6H_5)_2\}Pd(CH_3)(Cl)$,
$\{(PhCH_2)(t-Bu)NCH(Ph)P(C_6H_{11})_2\}Pd(CH_3)(Cl)$,
$\{(2\text{-pyridine})\ CH_2CH_2N(CH_3)CH(Ph)P(C_6H_5)_2\}Pd(CH_3)(Cl)$,
$\{PhN(CH_2CH_2)_2NCH(Ph)P(C_6H_5)_2\}Pd(CH_3)(Cl)$,
$\{NCCH_2CH_2N(CH_3)CH(Ph)P(C_6H_5)_2\}Pd(CH_3)(Cl)$,
$\{(PhCH_2)(CH_3)NCH(\text{ferrocenyl})P(C_6H_{11})_2\}Pd(CH_3)(Cl)$,
$\{(2,4,6\text{-}(CH_3)_3C_6H_2NCH(Ph)PPh_2\}_2Ti(CH_2Ph)_2$,
$\{(NCCH_2CH_2N(CH_3)CH(Ph)PPh_2\}MoCl_3$, $\{PhN(CH_2CH_2)_2NCH(Ph)PPh_2\}MoCl_3$,
$\{(PhCH_2)(CH_3)NCH(2\text{-pyridine})PPh_2\}FeCl_2$,
$\{(PhCH_2)(CH_3)NCH(2\text{-pyridine})PPh_2\}CoCl_2$,
$\{(PhCH_2)(CH_3)NCH(2\text{-pyridine})PPh_2\}NiBr_2$, and
$\{(PhCH_2)(CH_3)NCH(2\text{-pyridine})P(C_6H_{11})_2\}NiBr_2$.

The compounds of this invention are active catalysts, typically in combination with an activator. When an activator or activating technique is used, those of skill in the art may use alumoxanes, strong Lewis acids, compatible non-interfering activators and combinations of the foregoing. The foregoing activators have been taught for use with different metal complexes in the following references, which are hereby incorporated by reference in their entirety: U.S. Pat. Nos. 5,599,761, 5,616,664, 5,453,410, 5,153,157, 5,064,802, and EP-A-277,003. Preferred activators include methylalumoxane, trimethylaluminum, $AgBF_4$, $AgBPh_4$, $NaBAr'_4$, $H(OEt_2)_2BAr'_4$ and the like. An example of an activated complex of this invention is $\{(C_6H_{11})_2PCH(Ph)N(CH_3)(CH_2Ph)\}Pd(CH_3)(N\equiv CCH_3)^+BAr'_4{}^-$, where Ar is $3,5\text{-}(CF_3)_2(C_6H_3)$.

Ratios of neutral complex to activator are on the order of 1 to 1000 to 1000 to 1. More specifically, a ratio of about 1 to 1 is preferred. A scavenger can also be used with this invention. Scavengers useful herein include metal complexes, alumoxanes, aluminum alkyls and the like.

The catalysts herein may be used to polymerize ethylenically or acetylenically unsaturated monomers having from 2 to 20 carbon atoms either alone or in combination. Monomers include $C_2$ to $C_{20}$ α-olefins such as ethylene, propylene, 1-butene, 1-hexene, 1-octene, 4-mtheyl-1-pentene, styrene and mixtures thereof.

The compounds and catalysts of this invention usefully polymerize functionalized monomers, such as acetates and acrylates. Novel polymers, copolymers or interpolymers may be formed having unique physical and melt flow properties. Such novel polymers can be employed alone or with other polymers in a blend to form products that may be molded, cast, extruded or spun. End uses for the polymers made with the catalysts of this invention include films for packaging, trash bags, foams, coatings, insulating devices and household items. Also, such functionalized polymers are useful as solid supports for organometallic or chemical synthesis processes.

Polymerization can be carried out in the Ziegler-Natta or Kaminsky-Sinn methodology, including temperatures of from 0° C. to 400° C. and pressures from atmospheric to 3000 atmospheres. Suspension, solution, slurry, gas phase or high-pressure polymerization processes may be employed with the catalysts and compounds of this invention. Such processes can be run in a batch or continuous mode. Examples of such processes are well known in the art. A support for the catalyst may be employed, which may be alumina, silica or a polymers support. Methods for the preparation of supported catalysts are known in the art. Slurry, suspension, solution and high-pressure processes use a suitable solvent as known to those skilled in the art.

EXAMPLES

Unless otherwise noted, all experiments were performed in a Vacuum/Atmospheres glovebox under a nitrogen atmosphere. Anhydrous solvents in Sure-Seal bottles were purchased from Aldrich, sparged with nitrogen and stored over 4A molecular sieves in the glovebox. Aldehydes and amines were purchased from Aldrich and used without further purification. Phosphines and metal halides were purchased from Strem or Aldrich and used without further purification. (COD)PdMeCl was prepared from $(COD)PdCl_2$ (Strem) and $Me_4Sn$ in $CH_2Cl_2$. $NaBAr'_4$ and $H(OEt_2)_2BAr'_4$ were prepared by reported procedures (Brookhart et al, Organometallics, 1992, 11, 3920). NMR solvents were purchased from Cambridge Isotopes, sparged with nitrogen and stored over 4A molecular sieves. $^1H$ NMR data are reported in ppm and are referenced to residual protio solvent peaks ($CHD_5$: 7.15 ppm, $CHCl_3$: 7.24 ppm, and $CDHCl_2$: 5.32 ppm). $^{31}P$ NMR data are reported in ppm and are referenced to an external standard of 85% $H_3PO_4$. Elemental analyses were performed by QTI Laboratories, Whitehouse, N.J.

EXAMPLES 1–10

Examples 1–10 are examples of the preparation of aminomethylphosphine ligands (also referred to as "PCN" or generically $R^1R^2NCHR'PR^3R^4$). Each of these examples uses the same synthesis route, called method A, which is: In a glovebox, $R^3R^4PH$ (1.0–1.2 eq.), R'CHO (1.0–1.3 eq.), and $R^1R^2NH$ (1.0–1.3 eq.) were combined in THF (5–50 mL). The mixture was allowed to stir overnight at room temperature. THF was removed in vacuo, and the resulting oil or solid was dissolved in a minimal amount of pentane and recrystallized at −35° C. and dried in vacuo. Specific details for Examples 1–10 are as follows:

Example 1

$(PhCH_2)(CH_3)NCH(Ph)P(C_6H_{11})_2$. The reaction was set up as described in method A using 2.00 mL $(C_6H_{11})_2PH$ (9.90 mmol), 1.20 mL PhCHO(12.2 mmol), 1.30 mL $(PhCH_2)(CH_3)NH$(10.1 mmol) and 30 mL THF. 3.30 g (83%) of $(PhCH_2)(CH_3)NCH(Ph)P(C_6H_{11})_2$ was obtained as a colorless solid. $^{31}P$ $NMR(CDCl_3)\delta$—3.61.

Example 2

$(PhCH_2)(CH_3)NCH(Ph)P(C_6H_5)_2$. The reaction was set up as described in method A, using 2.00 mL $(C_6H_5)_2PH$(11.5 mmol), 1.20 mL PhCHO (12.2 mmol), 1.30 mL $(PhCH_2)(CH_3)NH$ (10.1 mmol) and 30 mL THF. Upon isolation of the crude product, a colorless solid was obtained which was washed with pentane (10 mL) and dried (2.97 grams). The pentane washings were cooled to −40° C. and an additional 0.66 gram of $(PhCH_2)(CH_3)NCH(Ph)P(C_6H_5)_2$ was collected. Total yield =3.63 g=77%. $^{31}P$ NMR $(CDCl_3)\delta$—17.15.

Example 3

(t-Bu)NHCH(Ph)P($C_6H_5$)$_2$. In a modification of method A, a large excess of t-BuNH$_2$ was used; specifically 2.00 mL ($C_6H_{11}$)$_2$PH(11.5 mmol), 1.18 mL PhCHO (12.0 mmol), 3.0 mL (t-BuNH$_2$(28.2 mmol).) and 20 mL THF were used. A colorless solid was obtained which was recrystallized from pentane (yield =2.97 g; 73%).

Example 4

(2,4,6-($CH_3$)$_3C_6H_2$)NHCH(Ph)P($C_6H_5$)$_2$. The reaction was set up as described in method A, using 0.350 mL ($C_6H_5$)$_2$PH(2.0 mmol), 0.200 mL PhCHO(2.0 mmol), 0.280 mL (2,4,6-($CH_3$)$_3C_6H_2$)NH$_2$(2.0 mmol) and 5 mL THF. Upon recrystallization, a colorless solid was obtained (yield =495 mg, 58%). $^{31}$P NMR (CDCl$_3$)δ3.81.

Example 5

($CH_3$)$_2$NCH$_2$CH$_2$N(CH$_3$)CH(Ph)P($C_6H_5$)$_2$. The reaction was set up as described in method A, using 0.350 mL ($C_6H_5$)$_2$PH(2.0 mmol), 0.210 mL PhCHO (2.1 mmol), 0.253 ($CH_3$)$_2$NCH$_2$CH$_2$NH(CH$_3$)(2.0 mmol) and 5 mL THF. A clear colorless oil resulted upon removal of THF; this oil was >95% pure by $^1$H NMR spectroscopy and was used without further purification (yield =504 mg, 67%).

Example 6

(PhCH$_2$)(CH$_3$)NCH(2-pyridine)P($C_6H_{11}$)$_2$. In a modification of method A, molecular sieves(4A) were added to the reaction mixture with 0.400 mL($C_6H_{11}$)$_2$PH (2.0 mmol), 0.190 mL pyridine-2-carboxaldehyde(2.0 mmol), 0.260 mL (PhCH$_2$)(CH$_3$)NH(2.0 mmol) and 5 mL THF. After 24 hours, the reaction mixture was filtered and THF was removed in vacuo. The resulting pink oil was recrystallized from pentane at −35° C., yielding a pink waxy solid(yield =527 mg; 65%). $^{31}$P NMR(CDCl$_3$) δ—1.57.

Example 7

(PhCH$_2$)(CH$_3$)NCH(2-pyridine)P($C_6H_5$)$_2$. In a modification of method A, molecular sieves(4A) were added to the reaction mixture with 0.700 mL($C_6H_5$)$_2$PH (4.0 mmol), 0.380 mL pyridine-2-carboxaldehyde(4.0 mmol), 0.520 mL (PhCH$_2$)(CH$_3$)NH(4.0 mmol) and 5 mL THF. After 24 hours, the reaction mixture was filtered and THF was removed in vacuo. The resulting pink oil was recrystallized from pentane at −35° C., yielding a pink waxy solid(yield =683 mg; 43%). $^{31}$P NMR(CDCl$_3$) δ—16.84.

Example 8

PhN(CH$_2$CH$_2$)$_2$NCH(Ph)P($C_6H_{11}$)$_2$. The reaction was set up as described in method, using 2.01 g($C_6H_{11}$)$_2$PH(10 mmol), 1.20 mL PhCHO(12.3 mmol), 1.52 g PhN(CH$_2$CH$_2$)$_2$NH(10.3 mmol) and 15 mL THF. After 24 hours, a colorless crystalline solid had formed in the reaction mixture. The solid was washed with pentane and dried in vacuo(yield =3.02 g; 70%). $^{31}$P NMR(CDCl$_3$)δ—1.57.

Example 9

PhN(CH$_2$CH$_2$)$_2$NCH(Ph)P($C_6H_5$)$_2$. The reaction was set up as described in method A, using 1.50 mL($C_6H_5$)$_2$PH(8.6 mmol), 1.20 mL PhCHO(12.3 mmol), 1.52 g PhN(CH$_2$CH$_2$)$_2$NH(10.3 mmol) and 10 mL THF. After 24 hours, the reaction mixture was concentrated to 5 mL, at which point crystals began to form. Pentane(10 mL) was added and the precipitate was collected, washed with pentane and dried. A second crop of crystals was collected by cooling the filtrate to −35° C.(combined yield =2.93 g; 98%).

Example 10

(NCCH$_2$CH$_2$)(CH$_3$)NCH(Ph)P($C_6H_5$)$_2$. The reaction was set up as described in method A, using 3.50 mL($C_6H_5$)$_2$PH (20.1 mmol), 2.30 mL PhCHO(23.4 mmol), 2.00 mL NCCH$_2$CH$_2$NH(CH$_3$)(21.4 mmol) and 10 mL THF. Upon removal of THF, a pale yellow oil was obtained. The oil was washed with 10 mL pentane, which caused it to solidify into a waxy off-white solid. The solid was dried in vacuo(yield =6.02 g; 86%).

EXAMPLES 11–13

Examples 11–13 are examples of the preparation of coordination complexes of certain PCN ligands with NiBr$_2$. Examples 11–13 used the following general synthesis procedure, called method B, which is: In a glovebox, solid NiBr$_2$(DME)(1.0 eq.) and the PNC ligand(1.0–1.2 eq.) were combined. CH$_2$Cl$_2$(5–20 mL) was added and the resulting generally red mixture was allowed to stir overnight. The mixture was then filtered and CH$_2$Cl$_2$ was removed in vacuo, yielding a generally dark red solid, which was washed with pentane and dried. Yields and specific details are as follows:

Example 11

{(PhCH$_2$)(CH$_3$)NCH(2-pyridine)P($C_6H_5$)$_2$}NiBr$_2$. Using method B, {(PhCH$_2$)(CH$_3$)NCH(2-pyridine)P($C_6H_5$)$_2$}NiBr$_2$ was prepared from (PhCH$_2$)(CH$_3$)NCH(2-pyridine)P($C_6H_5$)$_2$(212 mg, 0.54 mmol) and NiBr$_2$(DME)(135 mg, 0.44 mmol). The dark red product was recrystallized from CH$_2$Cl$_2$/pentane at −35° C. (185 mg; 68%). Anal: Calc. for C$_{26}$H$_{25}$N$_2$Br$_2$NiP:C; 53.47, H; 4.31, N, 4.80. Found: C, 55.49, H; 4.74, N; 4.89.

Example 12

{(PhCH$_2$)(CH$_3$)NCH(2-pyridine)P($C_6H_{11}$)$_2$}NiBr$_2$. Using method B, {(PhCH$_2$)(CH$_3$)NCH(2-pyridine)P($C_6H_{11}$)$_2$}NiBr$_2$ was prepared from (PhCH$_2$)(CH$_3$)NCH(2-pyridine)P($C_6H_{11}$)$_2$(161 mg, 0.40 mmol) and NiBr$_2$(DME) (125 mg, 0.40 mmol). A dark red microcrystalline powder was obtained.(95 mg, 38%) Anal: Calc. for C$_{26}$H$_{37}$N$_2$Br$_2$NiP: C; 51.66, H; 5.73, N; 4.30. Found: 51.41, H;6.27, N, 4.25.

Example 13

{(PhCH$_2$)(CH$_3$)NCH(Ph)P($C_6H_{11}$)$_2$}NiBr$_2$. Using method B, {(PhCH$_2$)(CH$_3$)NCH(Ph)P($C_6H_{11}$)$_2$}NiBr$_2$ was prepared from (PhCH$_2$)(CH$_3$)NCH(Ph)P($C_6H_{11}$)$_2$(417 mg, 1.02 mmol) and NiBr$_2$(DME)(312 mg, 1.01 mmol). The pink-red product was recrystalized from Et$_2$O/pentane at −35° C.(308 mg; 49%).

EXAMPLES 14–17

Examples 14–17 are examples of the preparation of coordination complexes of certain PCN ligands with Pd(CH$_3$)(Cl). Each of these examples used the same general synthesis procedure, called method C, which is: In a glovebox, solid (COD)Pd(CH$_3$)(Cl)(1.0–1.1 eq.) and the PCN ligand(1.0–1.1 eq.) were combined. Et$_2$O(5–50 mL) was added. After 10–30 minutes, a powder precipitated from solution. The powder was collected, washed with Et$_2$O and dried in vacuo. Specific details for each example are as follows:

Example 14

{(PhCH$_2$)(CH$_3$)NCH(Ph)P(C$_6$H$_{11}$)2}Pd(CH$_3$)(Cl). Following method C, {(PhCH$_2$)(CH$_3$)NCH(Ph)P(C$_6$H$_{11}$)$_2$}Pd(CH$_3$)(Cl) was prepared from(COD)Pd(CH$_3$)(Cl) (569 mg, 2.15 mmol) and(PhCH$_2$)(CH$_3$)NCH(Ph)P(C6H$_{11}$)2(825 mg, 2.02 mmol) in 40 mL of Et$_2$O.(yield: 810 mg, 72%) Anal: Calc'd for C$_{28}$H$_{41}$NClPPd: C; 59.78, H;7.31, N; 2.48. Found: C; 60.22, H; 7.34, N, 2.33.

Example 15

{(PhCH$_2$)(CH$_3$)NCH(Ph)P(C$_6$H$_5$)$_2$}Pd(CH$_3$)(Cl). Following method C, {(PhCH$_2$)(CH$_3$)NCH(Ph)P(C$_6$H$_5$)$_2$}Pd(CH$_3$)(Cl) was prepared from(COD)Pd(CH$_3$)(Cl) (264 mg, 1.0 mmol) and (PhCH$_2$)(CH$_3$)NCH(Ph)P(C$_6$H$_5$)$_2$(389 mg, 1.0 mmol) in 15 mL of Et$_2$O. (yield: 454 mg, 84%) Anal: Calc'd for C$_{28}$H$_{29}$NClPPd: C; 60.88, H;5.29, N; 2.54. Found: C; 60.65, H; 5.49, N, 2.16.

Example 16

{(PhCH$_2$)(CH$_3$)NCH(2-pyridine)P(C6H$_{11}$)2}Pd(CH$_3$)(Cl). Following method C, {(PhCH$_2$)(CH$_3$)NCH(2-pyridine)P(C6H$_{11}$)2}Pd(CH$_3$)(Cl) was prepared from (COD)Pd(CH$_3$)(Cl)(31 mg, 0.12 mmol) and (PhCH$_2$)(CH$_3$)NCH(2-pyridine)P(C6H$_{11}$)$_2$ (51 mg, 0.12 mmol) in 5 mL of Et$_2$O. (yield: 68 mg, 96%)

Example 17

{(PhCH$_2$)(CH$_3$)NCH(2-pyridine)P(C$_6$H$_5$)$_2$}Pd(CH$_3$)(Cl). Following a modified method C, {(PhCH$_2$)(CH$_3$)NCH(2-pyridine)P(C$_6$H$_5$)$_2$}Pd(CH$_3$)(Cl) was prepared from (COD)Pd(CH$_3$)(Cl) (105 mg, 0.40 mmol) and (PhCH$_2$)(CH$_3$)NCH(2-pyridine)P(C$_6$H$_5$)$_2$(156 mg, 0.39 mmol) in 5 mL of toluene. A beige solid precipitated from solution and was collected, washed with pentane and dried in vacuo. (yield: 194 mg; 90%) Anal: Calc'd for C$_{27}$H$_{28}$N$_2$ClPPd: C; 58.60, H; 5.10, N; 5.06. Found: C; 59.39, H; 5.25, N, 4.78.

EXAMPLES 18–21

Examples 18–21 are examples of the preparation of an active polymerization catalyst that can be characterized by the general formula {(PCN)Pd(CH$_3$)(NCCH$_3$)}$^+${BAr'$_4$}$^-$ (where Ar' is 3,5-(CF$_3$)$_2$(C$_6$H$_3$)). Example 18 used the complex of Example 14, Example 19 used the complex of Example 15, Example 20 used the complex of Example 16 and Example 21 used the complex of Example 17. Examples 18–21 each used the following preparation: In a glovebox, (PCN)Pd(CH$_3$)(Cl) (1.0 equiv), NaBAr'$_4$(1.0–1.1 equiv.) and CH$_3$CN (1–100 eq.) were combined. CH$_2$Cl$_2$ (1–50 mL) was added and the mixture was allowed to stir for 1 hour. The mixture was then filtered, and CH$_2$Cl$_2$ and CH$_3$CN were removed in vacuo, leaving a glassy solid. The solid was washed with pentane and dried in vacuo. Example 18 resulted in the formation of {(PhCH$_2$)(CH$_3$)NCH(Ph)P(C$_6$H$_{11}$)$_2$Pd(CH$_3$)(NCCH$_3$)}$^+${BAr'$_4$}$^-$. Example 19 resulted in the formation of {(PhCH$_2$)(CH$_3$)NCH(Ph)P(C$_6$H$_5$)$_2$Pd(CH$_3$)(NCCH$_3$)}$^+${BAr'$_4$}$^-$. Example 20 resulted in the formation of {(PhCH$_2$)(CH$_3$)NCH(2-pyridine)P(C$_6$H$_{11}$)$_2$Pd(CH$_3$)(NCCH$_3$)}$^+${BAr'$_4$}$^-$. Example 21 resulted in the formation of {(PhCH$_2$)(CH$_3$)NCH(2-pyridine)P(C$_6$H$_5$)$_2$Pd(CH$_3$)(NCCH$_3$)}$^+${BAr'$_4$}$^-$.

Other complexes prepared by the same procedure described for Examples 18–21 include {(CH$_3$)$_2$NCH$_2$CH$_2$N(CH$_3$)CH(Ph)P(C$_6$H$_5$)$_2$}Pd(CH$_3$)(CH$_3$CN)}$^+${BAr'$_4$}$^-$, {(PhCH$_2$)(t-Bu)NCH(Ph)P(C$_6$H$_{11}$)$_2$}Pd(CH$_3$)(CH3CN)}{BAr'4}$^-$, {(2-pyridine)CH$_2$CH$_2$N(CH$_3$)CH(Ph)P(C$_6$H$_5$)$_2$}Pd(CH$_3$)(CH$_3$CN)}$^+${BAr'$_4$}$^-$, {PhN(CH$_2$CH$_2$)$_2$NCH(Ph)P(C$_6$H$_5$)$_2$}Pd(CH$_3$)(CH$_3$CN)}$^+${BAr'$_4$}$^-$, {NCCH$_2$CH$_2$N(CH$_3$)CH(Ph)P(C$_6$H$_5$)$_2$}Pd(CH$_3$)(CH$_3$CN)}$^+${BAr'$_4$}$^-$, and {(PhCH$_2$)(CH$_3$)NCH(ferrocenyl)P(C$_6$H$_{11}$)$_2$}Pd(CH$_3$)(CH$_3$CN)}$^+${BAr'$_4$}$^-$.

EXAMPLES 22–117

Examples 22–117 are ligand synthesis examples. The syntheses were carried out in parallel using combinatorial chemistry techniques, as follows and using the chemicals set in Table 1, below. Each synthesis was set up by preparing 1.0 M solutions of the starting solutions in THF. A 96 well microtiter plate fitted with fritted glass wells was used. 4 A molecular sieves (appx. 40 mg/well) were dispensed into the plate using a solid dispensing plate. Each synthesis was carried out by placing about 500 μL of THF into each well of the microtiter plate, and then 100 μL of the phosphine solution (0.1 mmol) and 110 μL of the aldehyde and amine solutions (0.11 mmol) were added. The top of the microtiter plate was then covered with a sheet of TEFLON, a sheet of butyl rubber and a sheet of latex and then clamped to seal the microtiter plate. The plate assembly was then shaken gently overnight. The microtiter plate was then disassembled from the clamp assembly and transferred to a filter block. Fitrate from each well was collected in a 96 well microtiter plate, and each well of the reaction vessel was washed with 300 μL of THF. The solvent was then removed from the microtiter plate by blowing a steady stream of nitrogen and the microtiter plate was then dried in vacuo by placing it in the glovebox antechamber for about two hours.

Examples 22–117 used the following starting materials:

Starting Material Matrix for Examples 22-117

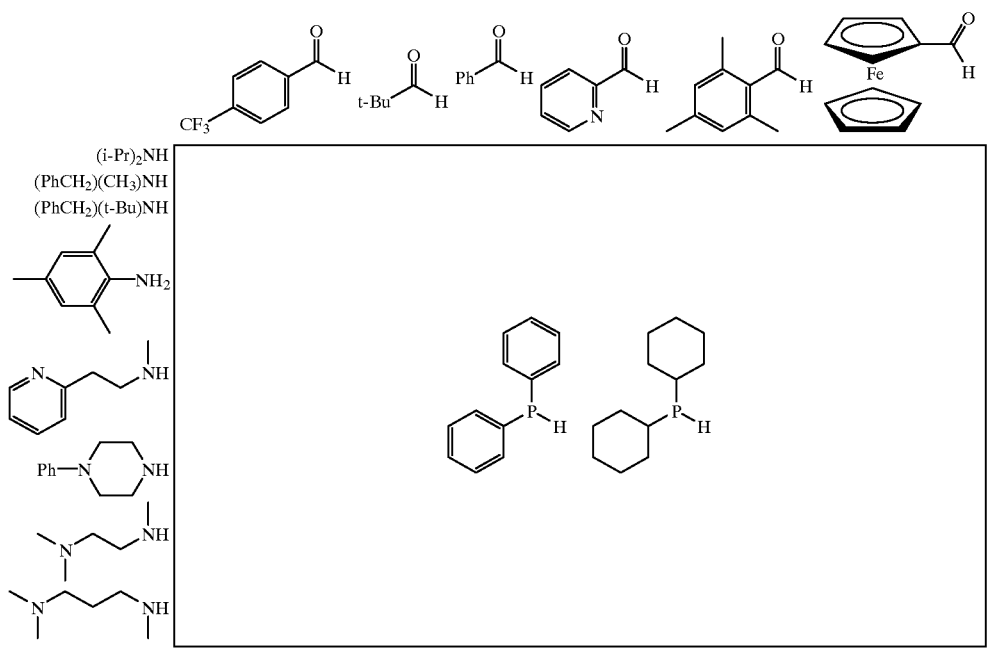

In 37 wells, partial or complete crystallization was observed after THF was removed. In 10 cases, the aminomethylphosphine ligands had been previously prepared by traditional solution chemistry and in all cases the morphology (crystalline or liquid) of those ligands prepared in the library matched that of the purified compounds. Selected elements of the library were then characterized by $^{31}$P NMR and were found to be the desired ligand. Use of these starting materials formed the following ligands:

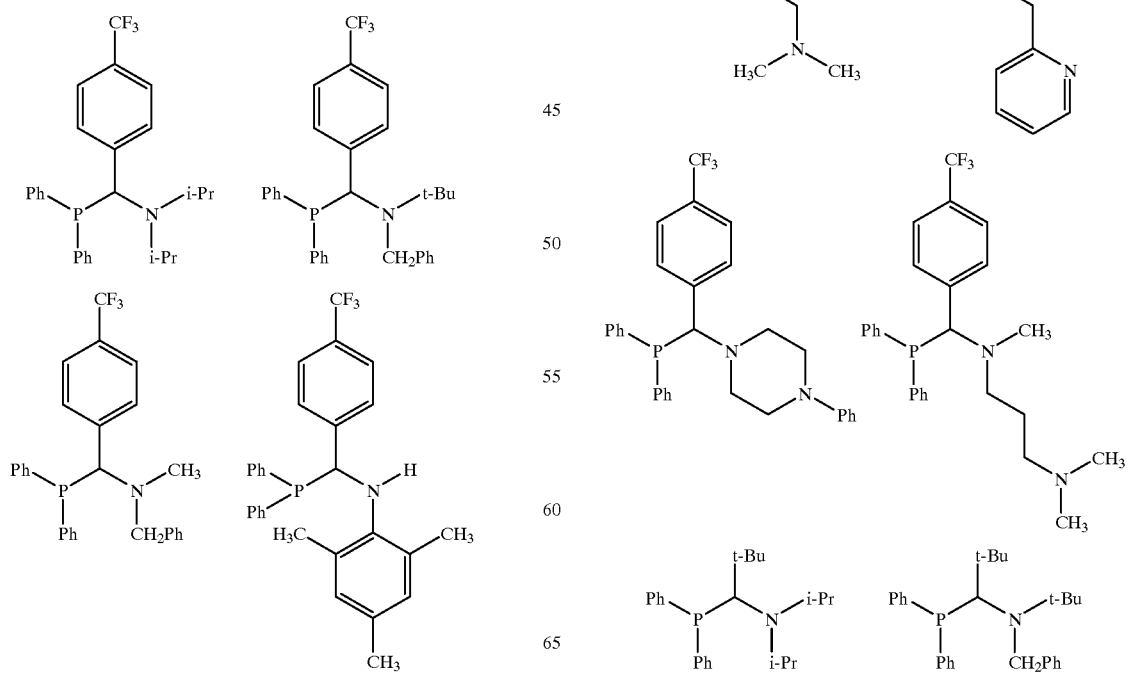

-continued
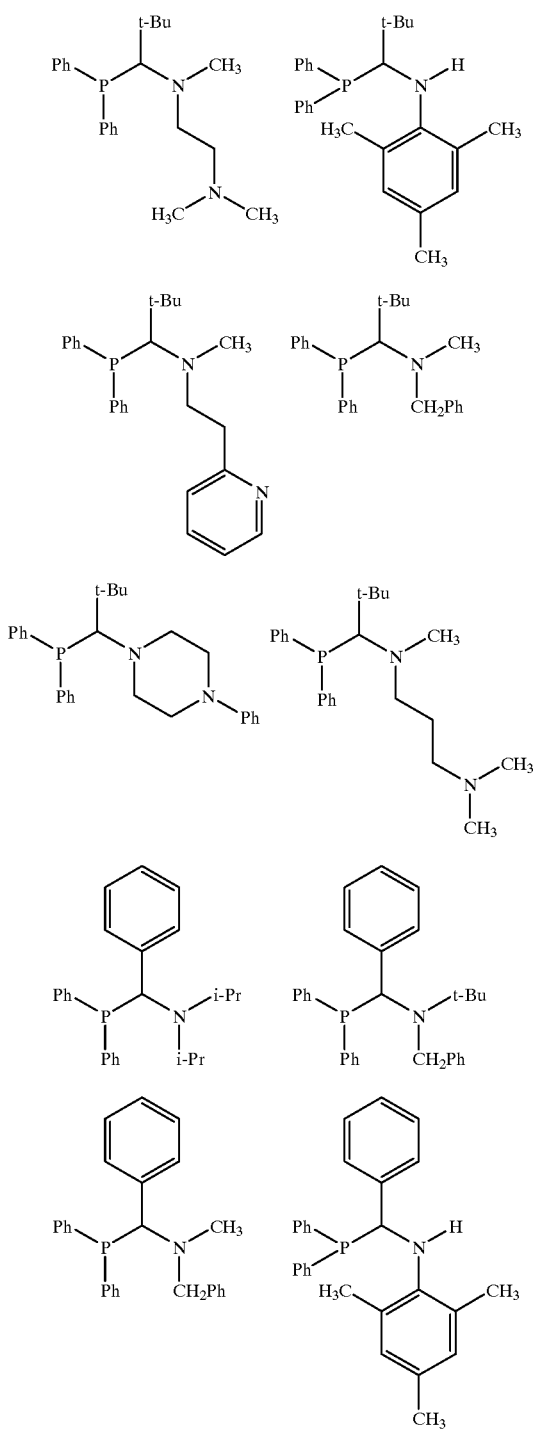
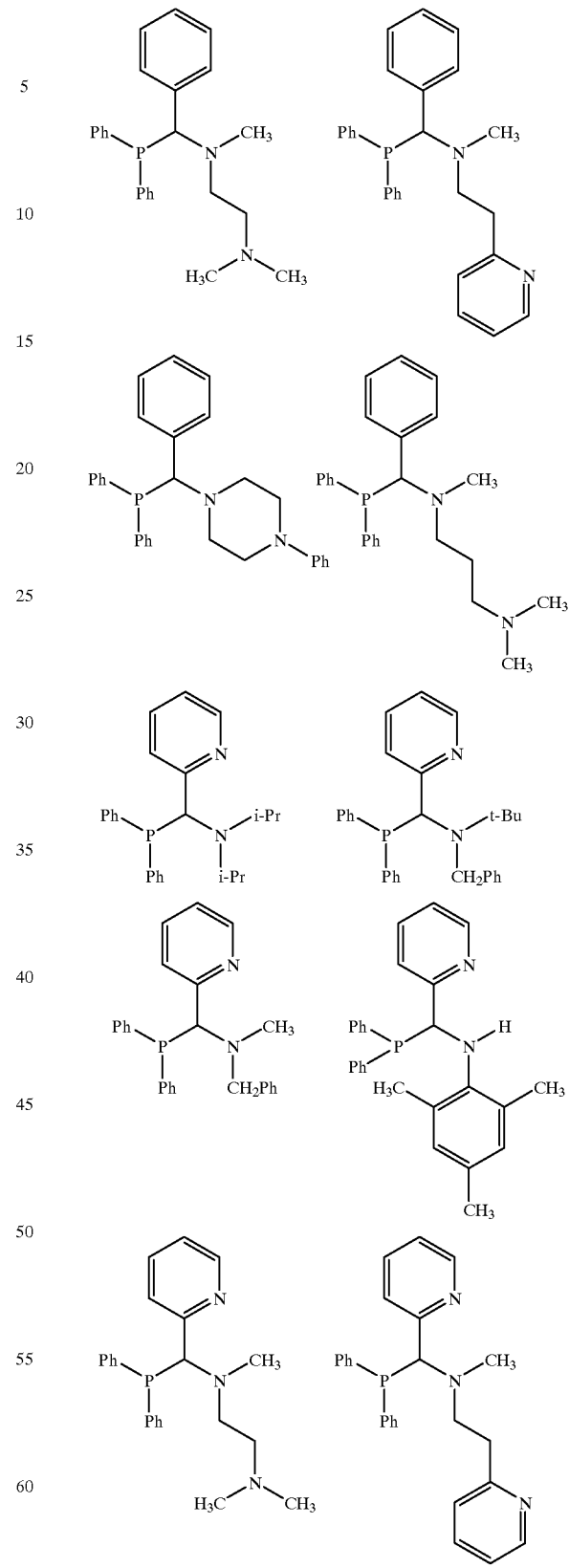

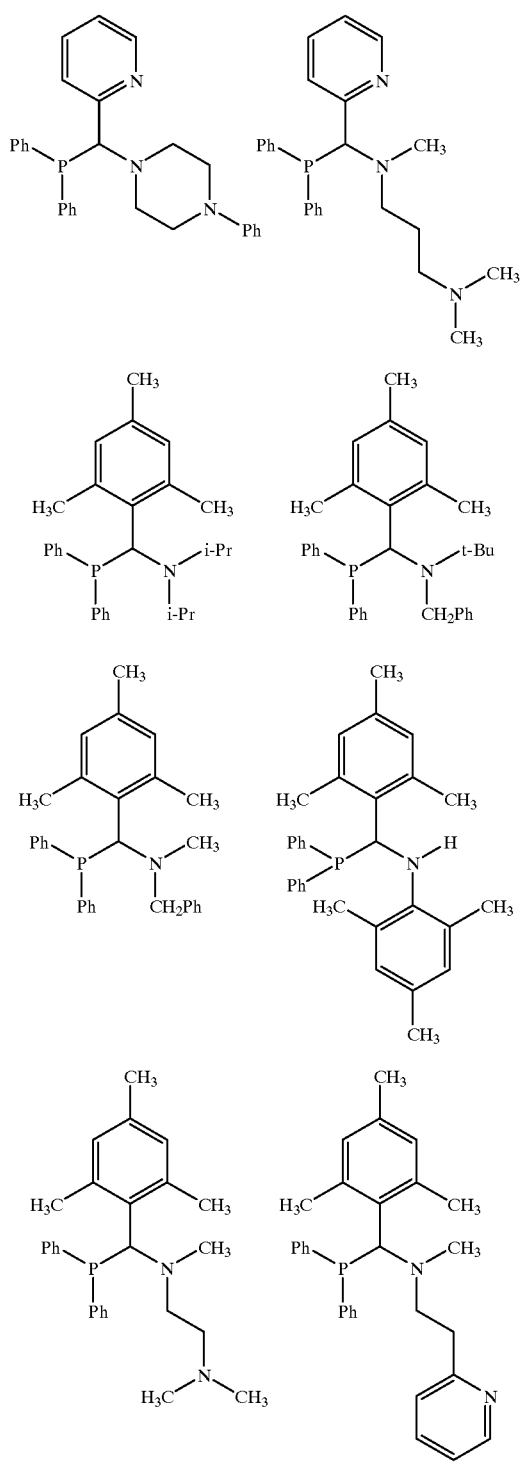
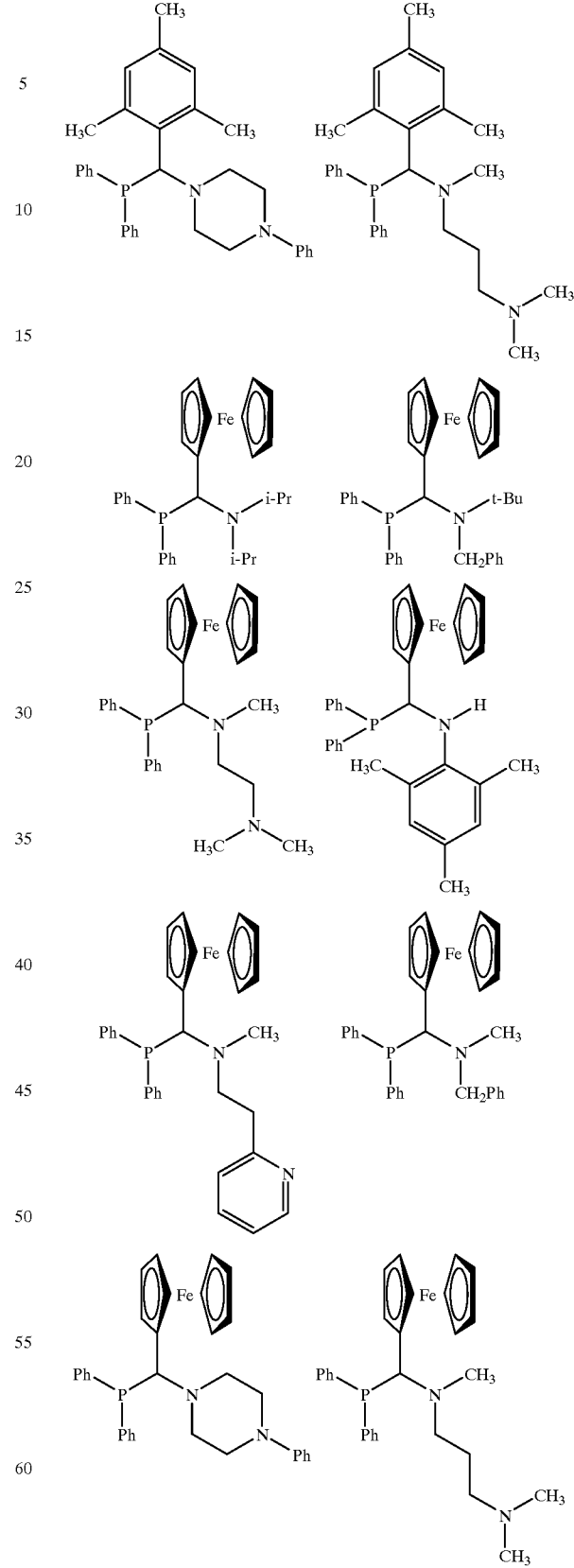

21
-continued
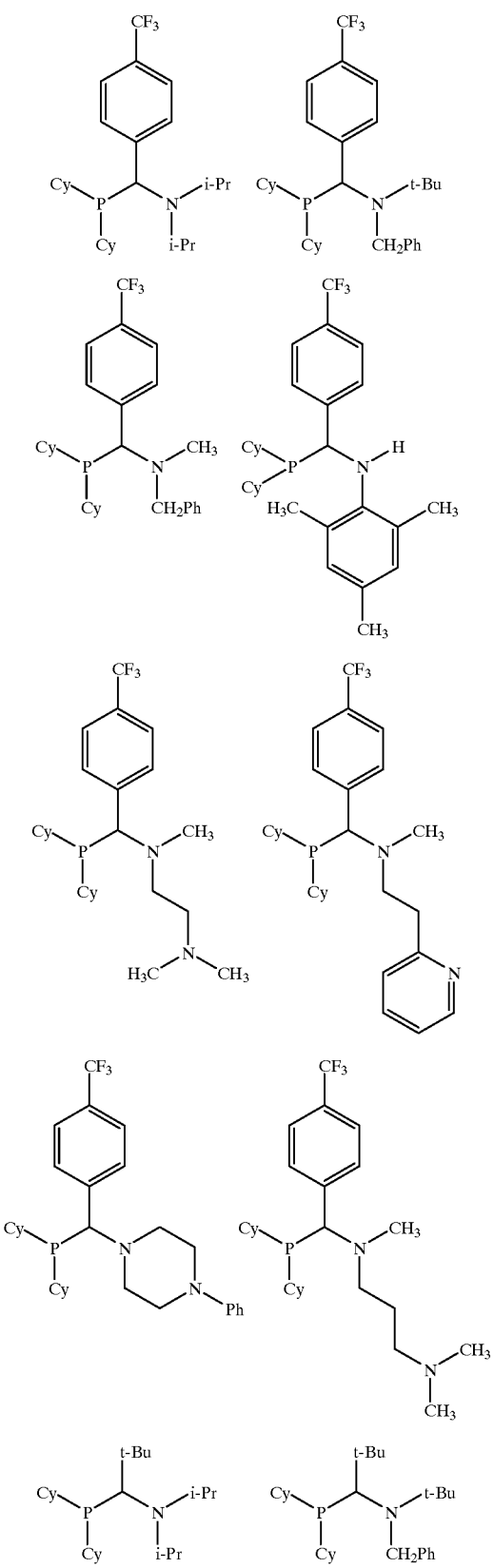
22
-continued
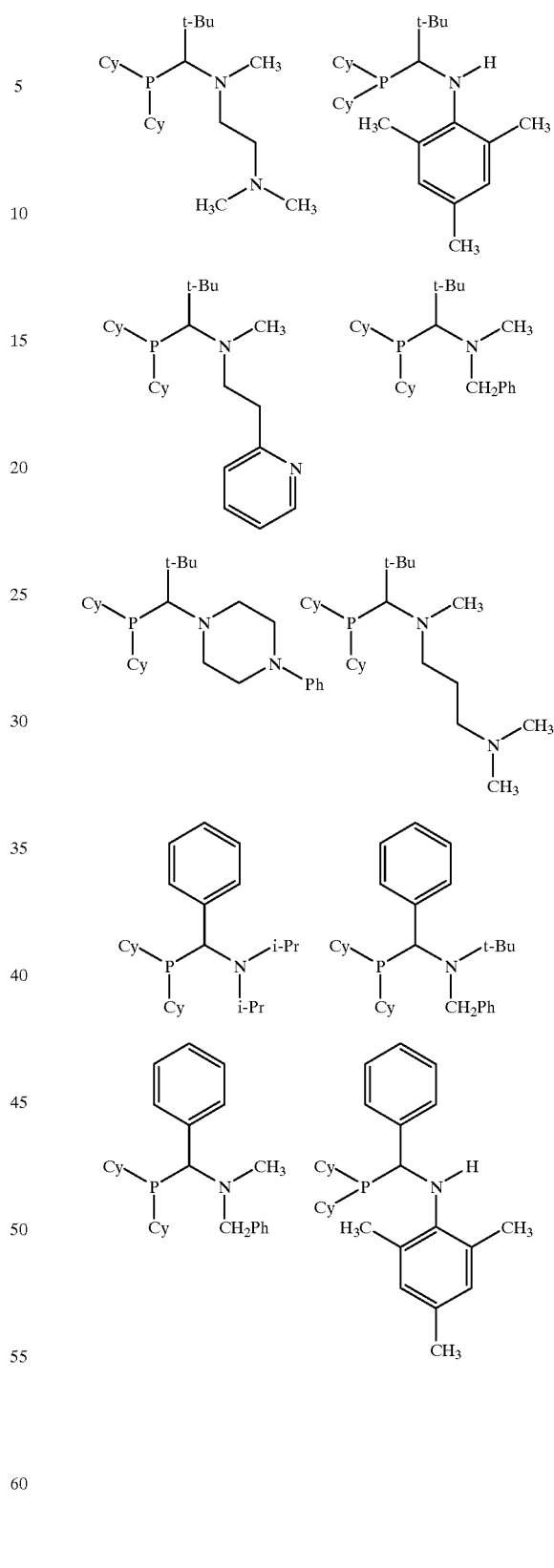

-continued
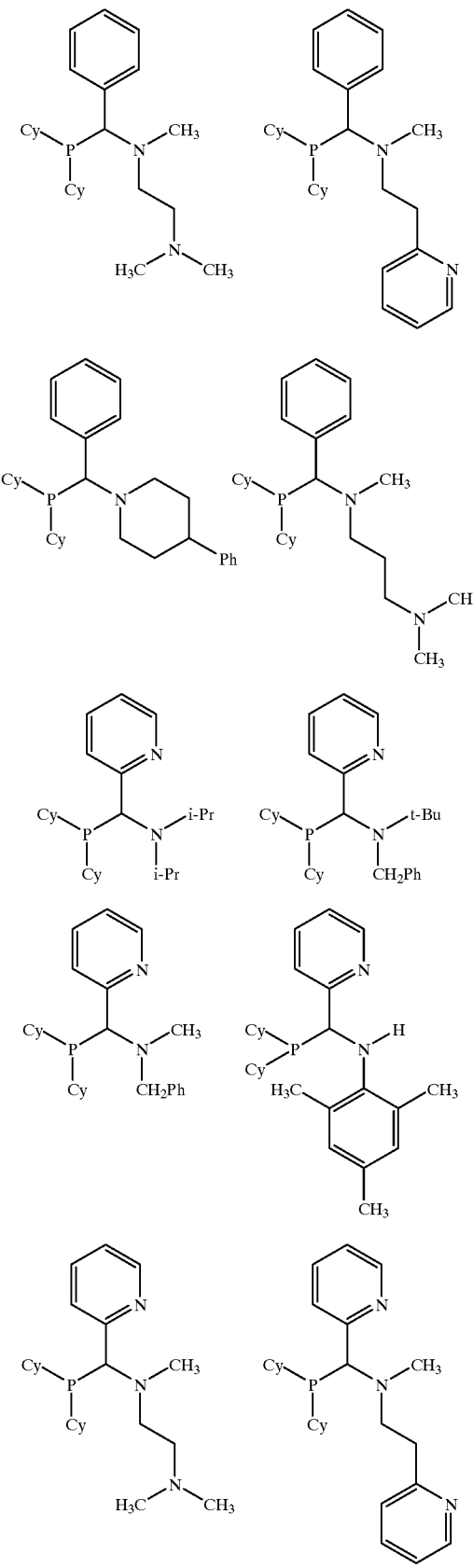
-continued
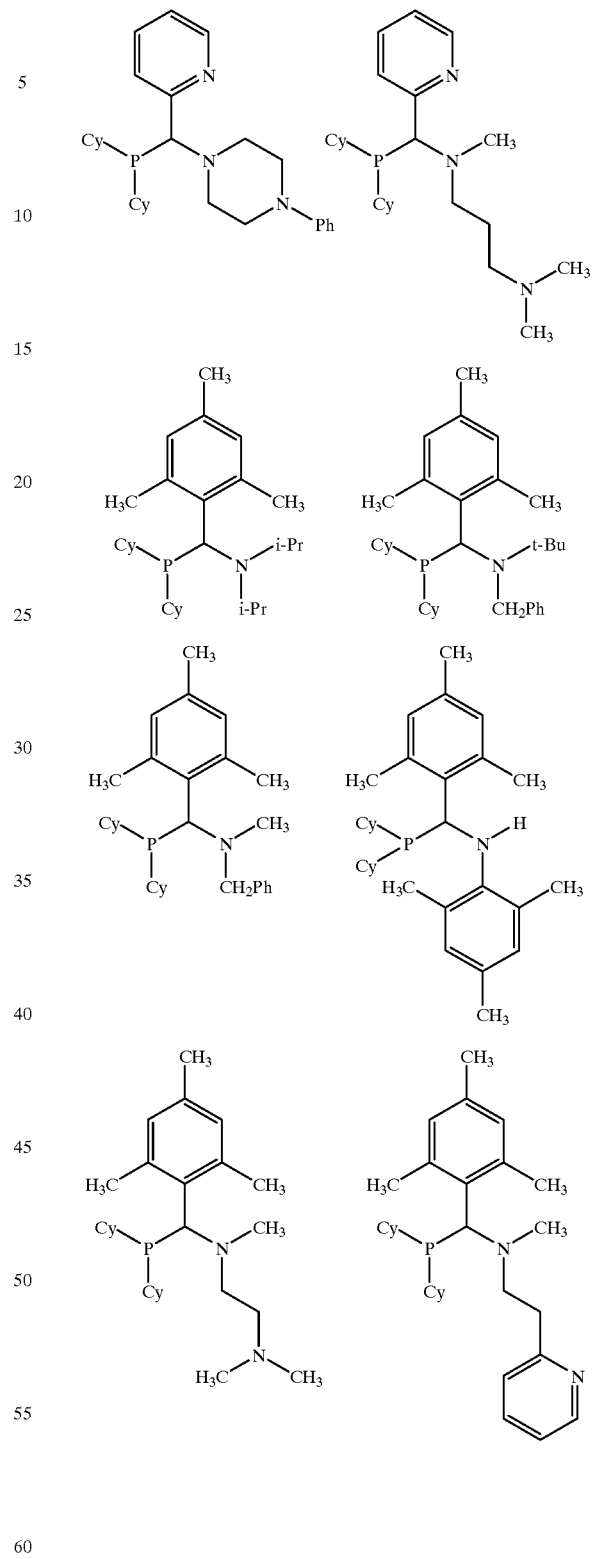

-continued

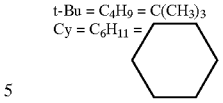

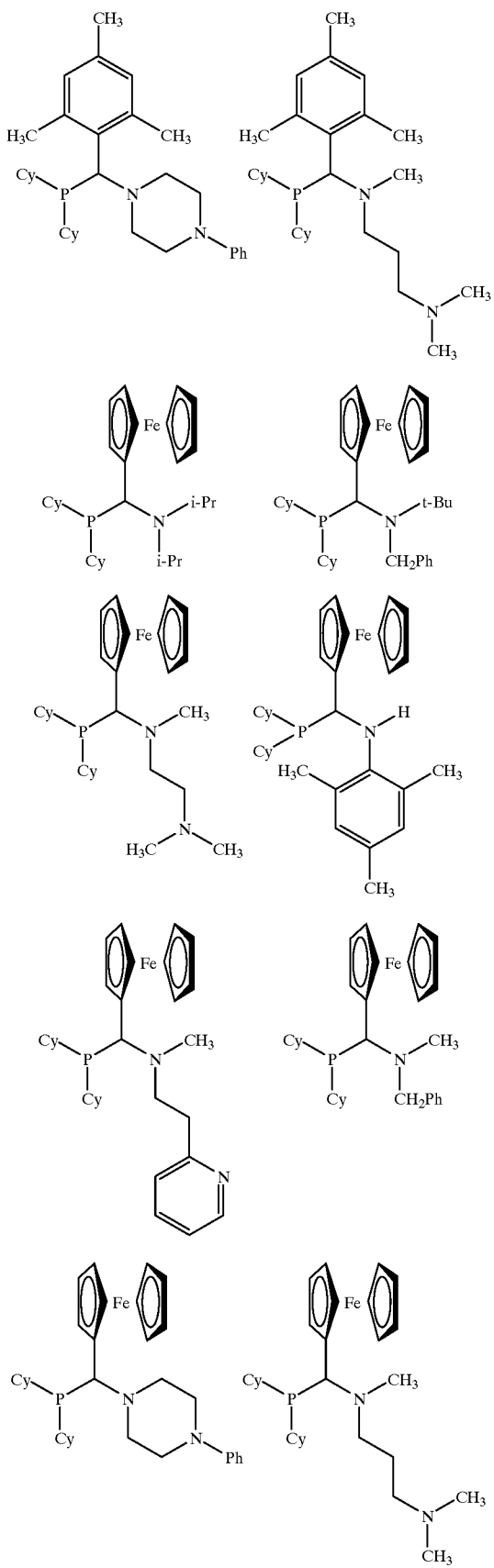

EXAMPLES 118–213

Preparation of a 96-Member Coordination Complex Library: Using the 96 ligands that were formed in Examples 22–117, coordination complexes were formed with each member. In a glovebox, 500 μL of $Et_2O$ was added to each element of the 96 member ligand library. 100 μL of a 0.50 M solution of CODPdMeCl (COD≡1,5-cyclooctadiene) in $CH_2Cl_2$(0.05 mmol) was then added to each well and the mixture was shaken for 1 hour. Pentane (500 μL) was added to each well and the microtiter plate was shaken for 10 minutes to precipitate the product. The contents of each well were then transferred by pipette to a filtering microtiter plate. The plate was filtered and each well was washed with pentane (1 mL). The contents of the microtiter plate were allowed to dry under a stream of $N_2$ and were stored in the glovebox. The color of the product ranged from dark red to colorless, and samples ranged from highly crystalline solids to powders to oily solids.

EXAMPLES 214–309

Generation of a 96-member library of $\{(PCN)Pd(CH_3)(NCCH_3)\}^+\{BAr'_4\}^-$. In a glovebox, $NaBAr'_4$(40 mg/well; 0.05 mmol) was loaded into a microtiter plate using a solid-addition plate. This microtiter plate (plate #1) was placed into a filter block, and the microtiter plate containing the 96-member library (from examples 118–213, plate #2) was placed on top of the filter block. 500 μL of $CH_2Cl_2$ was added to each well of plate #2 to dissolve solid the (PCN)PdMeCl. A vaccum was then applied to the filter block to transfer the contents of plate #2 into plate #1. Acetonitrile (40 μL) was then added to each well of plate #1 and the plate was then sealed in a manner similar to that described for Examples 22–117. The microtiter plate was shaken for 2 hours. The seal was then removed and solvent was removed by blowing nitrogen over the plate for 5 hours. The plate was then dried in vacuo for 2 hours.

Example 310

Polymerization of Ethylene: In a glovebox, $\{(PhCH_2)(CH_3)NCH(2\text{-pyridine})P(C_6H_5)_2Pd(CH_3)(NCCH_3)\}^+\{BAr'_4\}^-$(17 mg, 0.011 mmol) was dissolved in 20 mL $CH_2Cl_2$ and the solution was loaded into a 50 mL Schlenk flask. The flask was removed from the glovebox and placed under 7 psi of ethylene. The reaction was stirred for 4 hours. Solvent was removed in vacuo, leaving a waxy solid (120 mg) whose $^1H$ NMR spectrum matched that of polyethylene.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A compound characterized by the formula:

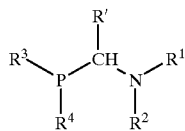

wherein each of $R^1$, $R^2$, $R^3$, and $R^4$ is, independently, selected from the group consisting of hydrogen, alkyl, substituted alkyl, aryl, substituted aryl, arylalkyl, substituted arylalkyl, acyl, halogen, amino, cyano, nitro, hydroxy, alkoxy, alkylamino, acylamino, silyl, germyl, stanyl, siloxy, phosphino, aryloxy, aryloxyalkyl, substituted aryloxyalkyl, heteroaryl, substituted heteroaryl, heteroarylalkyl, substituted heteroarylalkyl, heterocycles, substituted heterocycles, heterocyclicalkyl, substituted heterocyclicalkyl S-aryl and S-alkyl mercaptans and combinations thereof; and optionally $R^1$ and $R^2$ are combined together to form a ring structure and optionally, $R^3$ and $R^4$ are combined together in a ring structure;

R' is selected from the group consisting of substituted alkyl, substituted aryl, arylalkyl, substituted arylalkyl, acyl, halogen, cyano, nitro, hydroxy, alkylamino, acylamino, silyl, germyl, stanyl, siloxy, aryloxy, aryloxyalkyl, substituted aryloxyalkyl, heteroaryl, substituted heteroarylalkyl, substituted heteroarylalkyl, substituted heterocycles, heterocyclicalkyl, substituted heterocyclicalkyl S-aryl and S-alkyl mercaptans and combinations thereof.

2. A compound characterized by the formula:

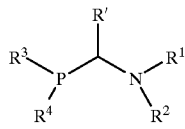

wherein each of $R^1$, $R^2$, $R^3$, and $R^4$ is, independently, selected from the group consisting of hydrogen, alkyl, substituted alkyl, saturated cyclic hydrocarbons, aryl, substituted aryl, arylalkyl, substituted arylalkyl, acyl, amino, alkylamino, acylamino, silyl, germyl, stanyl, siloxy, phosphino, aryloxy, aryloxyalkyl, substituted aryloxyalkyl, heteroaryl, substituted heteroaryl, heteroarylalkyl, substituted heteroarylalkyl, heterocycles, substituted heterocycles, heterocyclicalkyl, substituted heterocyclicalkyl, S-aryl and S-alkyl mercaptans and combinations thereof; and optionally $R^1$ and $R^2$ are combined together to form a ring structure and optionally, $R^3$ and $R^4$ are combined together in a ring structure; and R' is selected from the group consisting of aryl, substituted aryl, arylalkyl, substituted arylalkyl and combinations thereof.

3. The compound of claim 2, wherein $R^1$ and $R^2$ are, independently, selected from the group consisting of alkyl, substituted alkyl and saturated cyclic hydrocarbons.

4. The compound of claim 2, wherein $R^3$ and $R^4$ are, independently, selected from the group consisting of aryl, substituted aryl and saturated cyclic hydrocarbons.

5. A compound characterized by the formula:

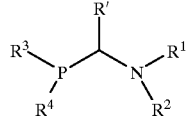

wherein each of $R^1$, $R^2$, $R^3$, and $R^4$ is, independently, selected from the group consisting of hydrogen, alkyl, substituted alkyl, saturated cyclic hydrocarbons, aryl, substituted aryl, arylalkyl, substituted arylalkyl, acyl, amino, alkylamino, acylamino, silyl, germyl, stanyl, siloxy, phosphino, aryloxy, aryloxyalkyl, substituted aryloxyalkyl, heteroaryl, substituted heteroaryl, heteroarylalkyl, substituted heteroarylalkyl, heterocycles, substituted heterocycles, heterocyclicalkyl, substituted heterocyclicalkyl, S-aryl and S-alkyl mercaptans and combinations thereof; and optionally $R^1$ and $R^2$ are combined together to form a ring structure and optionally, $R^3$ and $R^4$ are combined together in a ring structure; and R' is selected from the group consisting of benzyl, butyl, s-butyl, t-butyl, phenyl, 2,4,6-trimethylphenyl, 4-trifluoromethylphenyl, ferrocenyl, 2-pyridyl, 2-cyanophenyl, 3-cyanophenyl and 2-(diphenylphosphino)phenyl.

6. The compound of claim 5, wherein $R^1$ and $R^2$ are, independently, selected from the group consisting of alkyl, substituted alkyl and saturated cyclic hydrocarbons.

7. The compound of claim 5, wherein $R^3$ and $R^4$ are, independently, selected from the group consisting of aryl, substituted aryl and saturated cyclic hydrocarbons.

* * * * *

UNITED STATES PATENT AND TRADEMARK OFFICE
CERTIFICATE OF CORRECTION

PATENT NO.   : 6,034,240
DATED        : March 7, 2000
INVENTOR(S)  : LaPointe

It is certified that error appears in the above-identified patent and that said Letters Patent is hereby corrected as shown below:

Column 27,
Line 18, a comma should be inserted between "heterocyclicalkyl" and "S-aryl"
Line 27, the word -- substituted -- should be inserted before the word "heteroaryl,"
Line 27, "sub" should be deleted after the word "heteroaryl,"
Line 28, "stituted" should be deleted before the word "heteroarylalkyl"

Signed and Sealed this

Eleventh Day of February, 2003

JAMES E. ROGAN
*Director of the United States Patent and Trademark Office*